United States Patent [19]

Braun

[11] Patent Number: 4,854,317
[45] Date of Patent: Aug. 8, 1989

[54] APPLICATOR FOR C-SHAPED SCALP CLIPS

[75] Inventor: Karl Braun, Talheim, Fed. Rep. of Germany

[73] Assignee: Aesculap-Werke AG Vormals Jetter & Scheerer, Tutlingen, Fed. Rep. of Germany

[21] Appl. No.: 152,761

[22] Filed: Feb. 5, 1988

[30] Foreign Application Priority Data

Feb. 16, 1987 [DE] Fed. Rep. of Germany ....... 3704760

[51] Int. Cl.⁴ ...................... A61B 17/00; A61B 17/12; A61B 17/04
[52] U.S. Cl. ............................... 128/334 R; 128/325; 128/346; 29/243.56
[58] Field of Search ........................... 227/19, DIG. 1; 128/334 R, 325, 346; 29/243.56

[56] References Cited

U.S. PATENT DOCUMENTS 2,968,041 1/1961 Skold ............................ 227/DIG. 1
3,945,238 3/1976 Eckert .................................. 227/19
4,637,395 1/1987 Casper et al. ................... 128/334 R Primary Examiner—Edward M. Coven
Assistant Examiner—Gary Jackson
Attorney, Agent, or Firm—Kramer, Brufsky & Cifelli

[57] ABSTRACT

In an applicator for C-shaped scalp clips with applying instruments in the form of a movable edge and a stationary edge and with a retaining element for the scalp clips, the moved edge can be brought closer still to the stationary edge while the retaining element is fixed in its open position. When the direction of motion is reversed, the movable edge immediately takes the retaining element back with it into its locking position. The movable edge is thus coupled with the pivotable retaining element by a slip coupling.

4 Claims, 2 Drawing Sheets

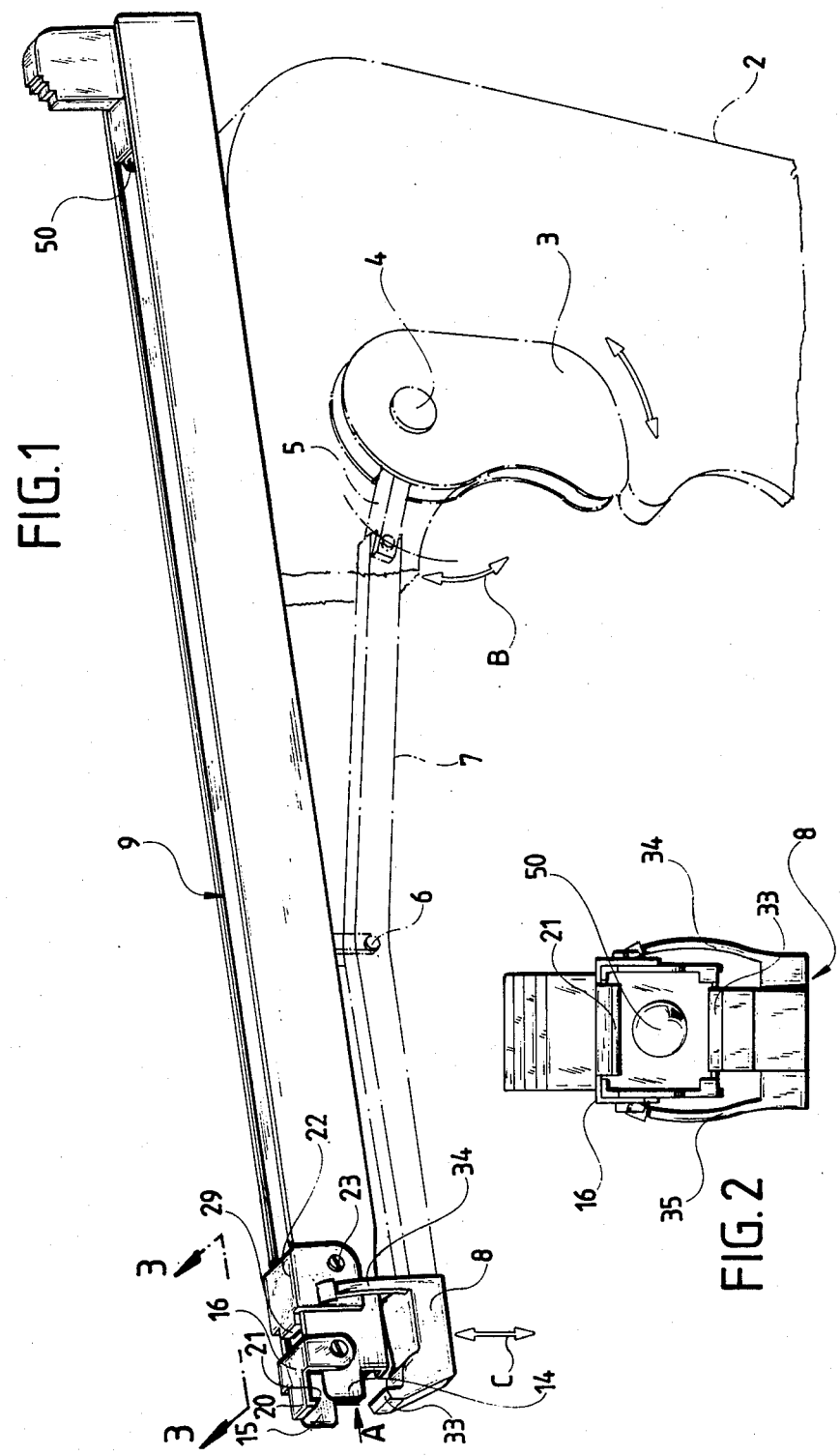

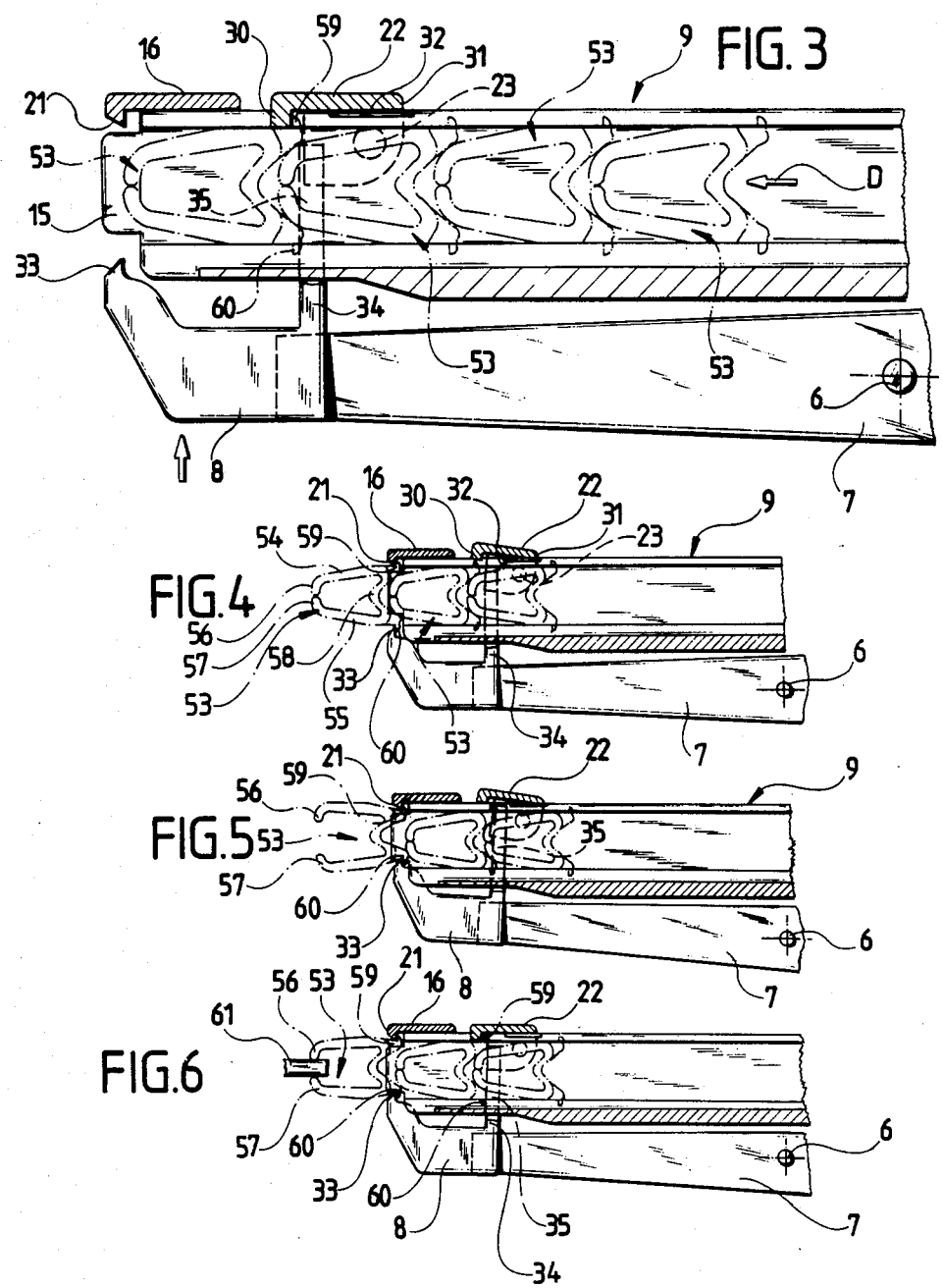

APPLICATOR FOR C-SHAPED SCALP CLIPS

BACKGROUND OF THE INVENTION

The invention relates to an applicator for C-shaped scalp clips having two legs joined by a bridge with clamping jaws facing each other at the free front ends of the legs and with rearwardly protruding application surfaces in the region where the legs and the bridge meet, comprising two applying instruments which can be applied to the application surfaces of a scalp clip and moved towards each other to open the scalp clip, namely a movable edge and a stationary edge, further comprising a magazine in which several scalp clips can be accommodated one behind the other such that the free ends of a scalp clip rest againt the bridge of the next scalp clip, the scalp clips being displaceable by an elastic energy storing means in the longitudinal direction of the magazine towards an open end of the magazine, the applying instruments, in a first position in which they are relatively far apart, protruding downwardly and upwardly into the path of advance of the scalp clips at the open end of the magazine, and a scalp clip which has been advanced past the applying instruments coming to rest at laterally protruding edge regions adjoining the application surfaces against the applying instruments, whereas, in a second position in which they are closer together, the applying instruments press on the application surfaces of the scalp clip held by them and bend it open, and also comprising a retaining element which is simultaneously pivotable together with the movable edge and which dips into the path of advance of the scalp clips and is displaceable out of it into an open position, the retaining element being arranged before the applying instruments by approximately the length of one scalp clip and holding back that scalp clip which follows directly behind the scalp clip gripped by the applying instruments.

In a known applicator of this kind (German Pat. No. 3,405,335) a manually actuatable lever which carries the movable edge acting as applying instrument is rigidly connected to the retaining element, and, therefore, the retaining element is forced to go through all of the motions of the movable edge as well. Consequently, when the scalp clps are spread open by the movable edge and the stationary edge coacting with it as further applying instrument, the retaining element in its open position is far away from that position in which it dips into the path of advance of the scalp clips in order to hold these back. Accordingly, when a piece of tissue is clamped in the scalp clip and the applying instruments assume an intermediate position, the retaining element has not yet returned to its closed position in which it safely secures following scalp clips. This may result in faulty operation of the applicator as scalp clips can pass the retaining element and emerge from the open end of the magazine in an undesired manner.

The object of the invention is to overcome this deficiency and to so improve a generic applicator that the retaining element already assumes its locking closed position when the movable edge used as applying instrument has not yet fully returned to its position of rest.

SUMMARY OF THE INVENTION

The object is accomplished, in accordance with the invention, by the movable edge being coupled with the pivotable retaining element by a slip coupling such that the moved edge can be brought closer still to the stationary edge while the retaining element is fixed in its open position, and when the direction of motion is reversed, the movable edge immediately takes the retaining element with it into its submerged position.

Accordingly, the retaining element already gets to its open position at the start of the motion of the movable edge and stays in it while the movable edge can move further still in the direction towards the spread open position of a scalp clip. However, once the reverse motion of the movable edge starts, the retaining element moves into is locking submerged position again and stays in it while the movable edge continues its return motion into the position of rest.

In this way, the scalp clips are always safely locked, with the exception of that operating phase in which advance of the scalp clips in the magazine is necessary.

It is advantageous for the retaining element to rest against a stop when in its open position. In the preferred embodiment of the invention, two claws protruding from a lever carrying the movable edge rest in a trailing, biased manner against side surfaces of the retaining element and take it along with them.

The following description of a preferred embodiment serves in conjunction with the appended drawings to explain the invention in further detail.

BRIEF DESCRIPTION OF THE DRAWINGS

FIG. 1 is a perspective view of an applicator;

FIG. 2 is a partial front view of the applicator in the direction of arrow A in FIG. 1;

FIG. 3 is a partial sectional view taken along line 3—3 in FIG. 1; and

FIGS. 4–6 are views similar to FIG. 3 showing various operating positions of the applicator.

DESCRIPTION OF THE PREFERRED EMBODIMENT

The applicator illustrated in the drawings comprises a handle 2 with an actuating grip 3 which is pivotable about an axis 4 in the direction of arrow B against the action of a spring by applying a finger of the hand spanning handle 2. Protruding from grip 3 is a short arm 5 which is articulatedly connected to a lever 7 which is pivotable about an axis 6 and carries at its free end an apparatus part 8 which can be moved up and down in the direction of arrow C by actuating grip 3. Fixedly connected to handle 2 is an elongated magazine 9 of U-shaped cross-section which is open at its front end located above apparatus part 8. At this end, the two side walls of the magazine end in protruding lugs 14, 15 which serve to laterally guide scalp clips, described below, which have been advanced in magazine 9. Fixedly arranged above the free, open end of magazine 9 is a U-shaped bridge 16. Its arm carries at its front end a downwardly bent lug 20 with a free edge 21 which forms a counter edge which dips into the crosssection of magazine 9.

A further U-shaped bridge 22 acting as retaining element is pivotably mounted by means of screws 23 on the upwardly open magazine 9 behind bridge 16. Protruding forwardly from the upper ram of bridge 22 is an extension 29 which carries a downwardly oriented retaining nose 30 (FIG. 3) at its free edge. In the position of rest of lever 7, illustrated in FIG. 3, the retaining nose 30 projects into the path of advance of scalp clips advanced in magazine 9. The bridge 22 with the retaining nose 30 can be pivoted out of the position illustrated in FIG. 3 into the open position illustrated in FIGS. 4 and 5 in which the retaining nose 30 is pivoted out of the path of advance. In this open position, the edge 31 of the pivotable bridge 22 located opposite nose 30 rests against a stop surface 32 in the form of a recess on the two upper lateral rims of magazine 9. This stop surface 32 delimits the pivotal motion of bridge 22 and defines the open position.

As shown in FIG. 3, the retaining nose 30 is set back by one scalp clip length relative to the edge 21 on the front, stationary bridge 16.

A movable edge 33 arranged on apparatus part 8 carried by lever 7, opposite edge 21, is relatively far away from edge 21 acting as counter edge when the apparatus is in the position of rest (FIGS. 1 and 3) and is brought closer to this edge by actuating grip 3 (FIG. 5). The width of movable edge 33 is such that it can enter between the two lugs 14,15 of magazine 9.

Protruding upwardly from apparatus part 8 carrying movable edge 33 are two claws 34, 35 which rest in a biased, trailing manner against the side walls of bridge 22 which forms a retaining element. The point at which claws 34, 35 rest against the side surfaces of the retaining element is chosen with respect to the screws 23 determining the axis of rotation of retaining element 22 such that when apparatus part 8 is moved upwardly, retaining element 22 is taken along in a rotating manner and moved into its open position by claws 34, 35. Once the rear edge 31 of retaining element 22 comes to rest against stop surface 32, the pivotal motion of the retaining element stops but as apparatus part 8 is moved further up, the claws can continue to move in a trailing manner at the side surfaces until the end position of movable edge 33 is reached. When the direction of motion of apparatus part 8 is reversed, claws 34, 35 immediately take retaining element 22 back into its position in which it dips into magazine 9 and which is defined by the upper bridge arm of the retaining element coming to rest against the upper rims of magazine 9. As apparatus part 8 moves down further, claws 34, 35 can then continue to move down in a trailing manner on the retaining element.

In this way, a kind of slip clutch is formed between the apparatus part 8 carrying movable edge 33 and the retaining element 22 by claws 34, 35 resting against the side surfaces of retaiing element 22. This function in such a way that as the movable edge 33 approaches edge 21, the retaining element immediately comes into its open position, but the movable edge 33 can still move closer to edge 21 while retaining element 22 is fixed in its open position, and when the direction of motion is reversed, the movable edge immediately takes the retaining element along with it into its position in which it is submerged in magazine 9.

The applicator is intended for accommodation of scalp clips 53 illustrated in dot-and-dash lines in the drawings. These scalp clips have an essentially C-shaped cross-section with two legs 54 and 55 which converge towards their free end and carry clamping jaws 56 and 57 at their free end. On the opposite side they are joined by a concave bridge 58. The scalp clips are preferably integrally made of resilient plastic and in the normal state are closed, the two clamping jaws 56, 57 then being pressed against each other.

When the apparatus is in operation, the scalp clips 53 are arranged one behind the other in magazine 9 such that the concave bridge side is remote from the applying instruments, i.e., stationary edge 21 and movable edge 33. The free ends of a clip lie in the concave recess of the bridge of the clip in front of it, as shown in FIG. 3. Provided at the end of the magazine remote from the applying instruments is a slider 50 which is displaceable along the magazine within it. By means of a coil spring which can be rolled up in the manner of a tape measure, the slider 50 advances the scalp clips arranged in the magazine in the direction towards applying instruments 21, 33 until the front scalp clip is prevented, on the one hand, by stationary edge 21 of bridge 16 and, on the other hand, by movable edge 33 of apparatus part 8 from advancing further. For this purpose, the scalp clips 53 have, in the region in which bridge 58 and legs 54, 55 meet, upwardly and downwardly protruding edges 59, 60 which strike stationary edge 21 and movable edge 33, respectively, as indicated in the case of the front scalp clip in FIG. 4. As this Figure also shows, the front scalp clip protrudes beyond the front end of magazine 9, and the laterally protruding lugs 14, 15 of the magazine (FIG. 1) guide the scalp clip laterally.

In the initial position of the apparatus, in accordance with FIG. 3, the retaining nose 30 of the pivotable bridge 22 rests agaiut the upper edge 59 of the first clip and thus prevents this clip and the clips behind it from being advanced by the spring-loaded slider 50.

To apply a scalp clip to a piece of tissue (scalp), proceeding from the initial position of the apparatus illustrated in FIG. 3, apparatus part 8 with movable edge 33 is moved upwardly by slight pivoting motion of actuating grip 3. The claws 34, 35 pressed agaiut the side surfaces of retaining element 22 take this element along with them and pivot it into its open position shown in FIG. 4. Since the front scalp clip 53 is now no longer held back, the whole row of scalp clips 53 arranged one behind the other can be advanced by the spring-loaded slider 50 in the direction of arrow D (FIG. 3) by one scalp clip length until the front clip is held at its protruding edges 59, 60 by stationary edge 21 and movable edge 33, respectively. In this position, the front scalp clip protrudes beyond the front end of magazine 9 ready to be applied.

By actuating the grip 3 and thereby pivoting it further, the movable edge 33 is now brought closer to edge 21 and the scalp clip is thereby opened, as shown in FIG. 5. The bridge 22 acting as retaining element remains in its open position with its rearward edge 31 resting against stop surface 32, while the two resilient claws 34, 35 can continue to slide upwardly at the side surfaces of this bridge (FIG. 5).

Once a piece of tissue 61 has been introduced between the open clamping jaws of the front scalp clip, the movable edge 33 is moved in the reverse direction by releasing actuating grip 3. During this return motion, the claws which are still pressed against the side surfaces of bridge 22 immediately guide the bridge back into its initial position in which retaining nose 30 engages behind the protruding edge 59 on the second scalp clip and thus secures the entire row of scalp clips in magazine 9 (FIG. 6).

The apparatus part 8 carrying the movable edge 33 similarly returns to its initial position and so the scalp clip holding the piece of tissue 61 can be released. In the last phase of this return motion, during which retaining element 22 is in its initial position, the claws connected to apparatus part 8 slide downwardly in a trailing manner at the side surfaces of this element and so the operating position illustrated in FIG. 3 is finally reached again and the procedure described above can be repeated.

When the apparatus is in the operating position shown in FIG. 6, the protruding edges 59, 60 on the front scalp clip are no longer quite so far apart on account of the piece of tissue 61 clamped between the clamping jaws 56, 57 as in the closed state of the scalp clip with the clamping jaws contacting each other (FIG. 3), and, therefore the front scalp clip holding the piece of tissue 61 can be released from the magazine before apparatus part 8 with the movable edge 33 has fully returned to its initial position, without the following scalp clip resting against it under the force of the spring.

What is claimed is:

1. An applicator for C-shaped scalp clips which have two legs joined by a bridge and facing clamping jaws at their front ends, rearwardly protruding application surfaces at the regions where the legs and bridge meet and laterally projecting edge regions adjoining the application surfaces, said applicator comprising:

two applying instruments having laterally protruding movable and stationary edges, respectively, for engaging the application surfaces of a scalp clip and moving towards each other to open said scalp clip;

a magazine for holding a plurality of scalp clips arranged one behind the other, with the free ends of one scalp clip resting against the bridge of the adjacent scalp clip, said magazine being open at the end to which the free ends of the legs of the scalp clips point;

an elastic energy storing means for displacing the scalp clips in the longitudinal direction towards the open end of said magazine;

said applying instruments, in a first position in which said instruments are apart from each other, protruding downwardly and upwardly into the advance path of said scalp clips at the open end of said magazine, such that the laterally projecting edge regions adjoining the application surface of the one of said scalp clips which has been advanced past said applying instruments by said elastic energy storing means rests against the laterally protruding movable and stationary edges of the applying instruments;

said applying instruments, in a second position being closer together than in said first position with said instruments pressing on the application surfaces of said one of said scalp clips held between them thereby bending said one of said scalp clips open, wherein the invention comprises:

a retaining element which is simultaneously pivotable together with said movable edge and which dips into the path of advance of said scalp clips and is displaceable out of said path into an open position, said retaining element being disposed before said applying instruments by approximately the length of one scalp clip and being operable to hold back a scalp clip which follows adjacent the scalp clip gripped by said applying instruments;

said retaining element being simultaneously pivotable together with said movable edge from an initial position, said movable edge being coupled with the pivotable retaining element by a slip coupling such that when said movable edge is brought closer to said stationary edge during movement of the instruments into an intermediate position between said first and second position, said retaining element is fixed in its open position, and when the instruments are moved to their first position, said movable edge immediately returns said retaining element to its submerged position.

2. An applicator as defined in claim 1, characterized in that in its open position, said retaining element (22) rests against a stop (32).

3. An applicator as defined in claim 1, characterized in that two claws (34,35) protrude from a lever (7) carrying said movable edge (33), said claws resting in a biased, trailing manner against side surfaces of said retaining element (22) and taking said retaining element along with them.

4. An applicator as defined in claim 2, characterized in that two claws (34,35) protrude from a lever (7) carrying said movable edge (33), said claws resting in a biased, trailing manner against side surfaces of said retaining element (22) and taking said retaining element along with them.

* * * * *